US010153321B2

(12) United States Patent
Verbakel et al.

(10) Patent No.: US 10,153,321 B2
(45) Date of Patent: Dec. 11, 2018

(54) RADIATION DETECTOR CORE ASSEMBLY AND METHOD FOR CONSTRUCTING THE SAME

(71) Applicant: KONINKLIJKE PHILIPS N.V., Eindhoven (NL)

(72) Inventors: Frank Verbakel, Helmond (NL); Peter Van Delft, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 12 days.

(21) Appl. No.: 15/525,090

(22) PCT Filed: Nov. 6, 2015

(86) PCT No.: PCT/EP2015/075867
§ 371 (c)(1),
(2) Date: May 8, 2017

(87) PCT Pub. No.: WO2016/078930
PCT Pub. Date: May 26, 2016

(65) Prior Publication Data
US 2017/0317133 A1  Nov. 2, 2017

(30) Foreign Application Priority Data
Nov. 20, 2014  (EP) .................................... 14193976

(51) Int. Cl.
*H01L 27/14*  (2006.01)
*H01L 31/02*  (2006.01)
(Continued)

(52) U.S. Cl.
CPC ........ *H01L 27/14661* (2013.01); *A61B 6/032* (2013.01); *A61B 6/4233* (2013.01);
(Continued)

(58) Field of Classification Search
CPC ......... H01L 27/14661; H01L 27/14618; H01L 27/14634; H01L 27/14636;
(Continued)

(56) References Cited

U.S. PATENT DOCUMENTS 7,223,981 B1  5/2007 Capote
7,700,923 B2  4/2010 Green
(Continued)

FOREIGN PATENT DOCUMENTS

JP  2012118050  6/2012
KR  20130039177  4/2013
(Continued)

OTHER PUBLICATIONS

Kang, et al., "Feasibility study of direct-conversion x-ray detection using cadmium zinc telluride films", Journal of Instrumentation, vol. 7, Jan. 2012.

*Primary Examiner* — Didarul Mazumder

(57) ABSTRACT

The present invention is directed towards a moisture resistant radiation detector core assembly which was constructed by first assembling the photon-electron conversion layer, integrated circuit and the connection elements between and then encapsulating the whole assembly. This provides improved moisture barrier properties, since the encapsulation also covers the connection elements and does not have to be opened to apply the electrical connections, as is done for known radiation detector core assemblies.

14 Claims, 4 Drawing Sheets

(51) Int. Cl.
*A61B 6/03* (2006.01)
*A61B 6/00* (2006.01)
*C09D 165/04* (2006.01)
*C09K 11/88* (2006.01)
*H01L 27/146* (2006.01)
*H01L 31/0296* (2006.01)
*H01L 31/024* (2014.01)

(52) U.S. Cl.
CPC .......... *C09D 165/04* (2013.01); *C09K 11/883* (2013.01); *H01L 27/1469* (2013.01); *H01L 27/14618* (2013.01); *H01L 27/14634* (2013.01); *H01L 27/14636* (2013.01); *H01L 27/14659* (2013.01); *H01L 27/14696* (2013.01); *H01L 31/02966* (2013.01); *H01L 31/024* (2013.01); *H01L 2224/16145* (2013.01); *H01L 2224/48091* (2013.01); *H01L 2224/48247* (2013.01)

(58) Field of Classification Search
CPC .......... H01L 27/14659; H01L 27/1469; H01L 27/14696; H01L 31/02966; H01L 31/024; A61B 6/032; A61B 6/4233; C09D 165/04; C09K 11/883

USPC .......................................... 257/292; 438/48
See application file for complete search history.

(56) References Cited

U.S. PATENT DOCUMENTS

| | | | |
|---|---|---|---|
| 7,871,860 | B1 | 1/2011 | Pu |
| 7,955,992 | B2 | 6/2011 | Chen |
| 2008/0149844 | A1* | 6/2008 | Chen .................... G01T 1/2928 250/370.13 |
| 2010/0032579 | A1 | 2/2010 | Chen |
| 2012/0288688 | A1 | 11/2012 | Kug |
| 2013/0168555 | A1 | 7/2013 | Moon |
| 2013/0330498 | A1* | 12/2013 | Hogg .................... A61N 1/375 428/76 |
| 2014/0175299 | A1* | 6/2014 | Spahn .................... G01T 1/247 250/394 |

FOREIGN PATENT DOCUMENTS

| | | |
|---|---|---|
| WO | 03/019659 | 3/2003 |
| WO | 2010/088066 | 8/2010 |

* cited by examiner

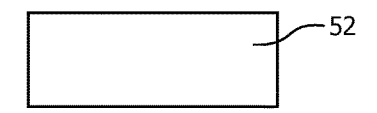
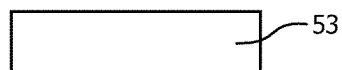
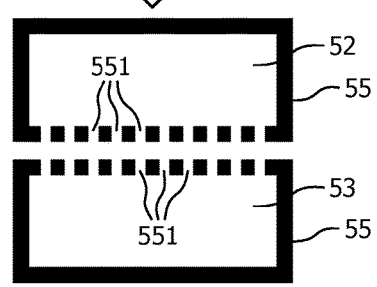
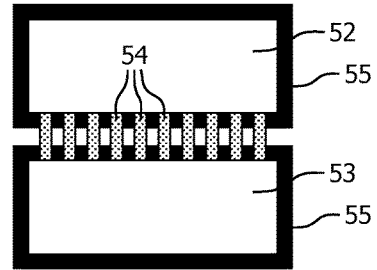
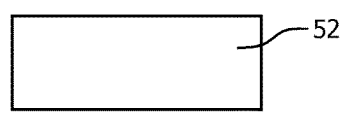
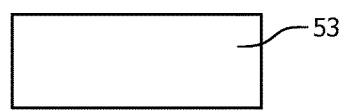
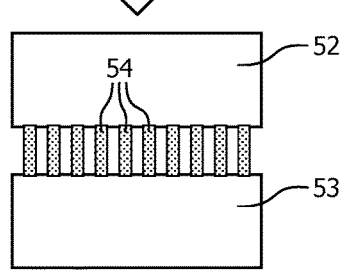
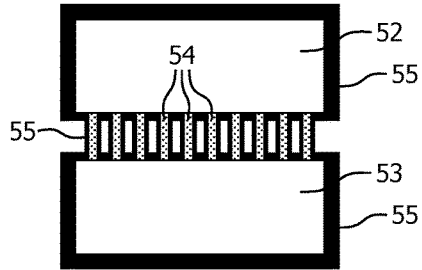
FIG. 4a  FIG. 4b

RADIATION DETECTOR CORE ASSEMBLY AND METHOD FOR CONSTRUCTING THE SAME

CROSS REFERENCE TO RELATED APPLICATIONS

This application is the U.S. National Phase application under 35 U.S.C. § 371 of International Application No. PCT/EP2015/075867, filed Nov. 6, 2015, published as WO 2016/078930 on May 26, 2016, which claims the benefit of European Patent Application Number 14193976.9 on Nov. 20, 2014. These applications are hereby incorporated by reference herein.

FIELD OF THE INVENTION

The present invention generally relates to a method for constructing a radiation detector core assembly, a radiation detector core assembly, a radiation detector, a radiation imaging device and a computed tomography imaging system.

BACKGROUND OF THE INVENTION

A direct conversion radiation detector, as used in, for instance, computed tomography (CT) imaging, detects radiation by directly converting incoming radiation into electrical signals, which may, amongst others, be used for photon counting. Direct conversion detectors, and particularly those with a Cadmium Zinc Telluride (CdZnTe or CZT) direct conversion layer, are sensitive to moisture. Over time, exposure to moisture may change properties of a photon-electron conversion layer and a surface of the direct conversion detector. This may result in an increase of leakage current, which negatively influences photon counting properties of the direct conversion detector. Also other direct conversion materials, e.g. Cadmium Telluride or (other) single crystal materials, are similarly influenced by moisture.

In a shorter time frame moisture may cause a short circuit between a cathode and an anode via a direct conversion layer surface, which almost certainly will destroy the detector's integrated circuit (ASIC) and sensor. Furthermore, moisture in the direct conversion layer in combination with high used voltages in the device may cause an increased chance of breakdown.

And, moisture sensitivity in the radiation detector is not exclusive to the direct conversion layer. Also properties of other components, such as electrodes and connects, may be adversely affected by moisture. For the same reason the problem also extends to non-direct conversion radiation detectors. On top of that, non-direct conversion radiation detectors with scintillator materials, such as Cesium Iodide, may likewise have similar moisture sensitivity and the related problems associated with this.

To prevent moisture degradation, encapsulation is applied to the direct conversion detector. Encapsulation not only reduces moisture degradation, it may also improve scratch resistance and chemical resistance of the detector and its components. Encapsulation may be achieved by providing a liquid encapsulation layer to the detector, for instance by applying an epoxy-based material. Such liquid encapsulation materials are commonly applied to a detector (CZT) tile with electrodes and afterwards openings are formed on detector pixels for contacting by photolithography. Application of the encapsulation is troublesome as good coverage of the corners and edges is difficult to obtain when using a liquid based material.

As an alternative other encapsulation materials, including $SiO_2$, AlN, SiN and $Al_2O_3$ are known that are not applied as a liquid, but using physical vapor deposition ('sputtering') or chemical vapor deposition (CVD). These processes cause the substrate, including the direct conversion material, to be heated up. With sputtering the substrate may heat up to 100 to 150 degrees Celsius. For CVD the substrate is exposed to 200 to 700 degrees Celsius. These processing temperatures are too high for use with the direct conversion material, because this will negatively influence the properties of the direct conversion material (such as single crystal properties of CZT). The temperature should not exceed 100 degrees Celsius, preferably not 80 degrees Celsius for extended periods of time. It is possible to perform CVD at a lower temperature, e.g. at 100 degrees Celsius, but this results in an insufficient moisture barrier, because pinholes, insufficient layer build-up and other defects are much more prevalently present. Said maximum processing temperature is especially important for detector tiles of those used in CT detectors, since any (material) defects may influence the fast sensor operation required for CT.

In U.S. Pat. No. 7,700,923 B2, and in other publications, parylene, an organic polymer, is disclosed as an encapsulation material, which is deposited from the gas phase at room temperature to form a layer with good humidity barrier properties.

However, a problem with parylene, and the other encapsulant materials, is that after encapsulation a lithographical step is required to locally open the encapsulation material to allow for connecting detector pixels to the ASIC. The encapsulation is therefore not fully conformal, somewhat limiting the moisture barrier, as well as chemical and mechanical resistance.

SUMMARY OF THE INVENTION

Embodiments according to the present invention are directed to a method for constructing a radiation detector core assembly comprising the steps of assembling a radiation detector core assembly from a photon-electron conversion element, an integrated circuit and at least one connection element located between and mechanically connecting the photon-electron conversion element with the integrated circuit; and depositing a gaseous encapsulation material onto the assembled detector core assembly on all outer surfaces of at least the photon-electron conversion element and all of the at least one electrical connection elements at a temperature below 100 degrees. As such a radiation detector core assembly is obtained that has an improved moisture barrier, since the connections are encapsulated as well and in the same step as the other components. It is not necessary to create openings in the encapsulation as in the known radiation detector core assembly.

Another embodiment of the present invention is directed towards keeping the temperature below 60 degrees Celsius, preferably room temperature. This prevents thermal degradation and mechanical deformation in the radiation detector core assembly.

A further embodiment of the present invention is directed towards the gaseous encapsulation material being a parylene precursor material that forms a parylene encapsulation layer on the assembled detector core assembly during or after the depositing step. Further embodiments are directed towards the parylene precursor material being an, optionally substituted, p-xylylene radical monomer that is preferably formed from thermal decomposition of p-cyclophane. A further embodiment of the present invention is directed towards the parylene precursor material being formed in a reaction chamber that is controllably connected to a deposition chamber in which the deposition step is performed. Parylene is particularly useful as an encapsulant, since it may be processed from the gas-phase and provides a conformal, encapsulation with good moisture barrier properties. It may be produced from precursors in a reaction chamber connected to the deposition chamber to allow for the formation of fresh parylene with less chance of it having reverted to dimers or polymers.

A further embodiment of the present invention is directed towards the at least one connection element comprising an electrical connection element that electrically connects the photon-electron conversion element with the integrated circuit, such as a solder ball or a metal filled epoxy drop, and/or an optical connection element that optically connects the photon-electron conversion element with the integrated circuit. The connection element is not only mechanically connecting the photon-electron element with the integrated circuit; it is usually also part of transferring electrons or photons between the several layers.

A further embodiment of the present invention is directed towards the photon-electron conversion element at least substantially consisting of a direct conversion material, preferably a Cadmium Telluride material and more preferably a Cadmium Zinc Telluride material. These materials are important in photon counting detectors, but are particularly sensitive to moisture and would particularly benefit from the method of the present invention.

The invention is further directed towards a moisture resistant radiation detector core assembly obtainable by the methods mentioned above, a radiation detector comprising such a detector core assembly, and a radiation imaging device and a computed tomography imaging system comprising such a radiation detector core assembly.

Still further aspects and embodiments of the present invention will be appreciated by those of ordinary skill in the art upon reading and understanding the following detailed description. Numerous additional advantages and benefits will become apparent to those of ordinary skill in the art upon reading the following detailed description of preferred embodiments.

BRIEF DESCRIPTION OF THE DRAWINGS

The present invention is illustrated by drawings of which

FIG. 4 shows a schematic representation of a method to encapsulate a radiation detector according to the prior art (FIG. 4a) and according to the present invention (FIG. 4b).

The invention may take form in various components and arrangements of components, and in various process operations and arrangements of process operations. The drawings are only for the purpose of illustrating preferred embodiments and are not to be construed as limiting the invention. To better visualize certain features may be omitted or dimensions may be not be according to scale.

DETAILED DESCRIPTION OF EMBODIMENTS

The present invention finds particular use in (medical) radiation imaging devices and is explained using computed tomography, but the invention is also applicable to other imaging devices in which a radiation detector is used, especially when a direct conversion radiation detector is used.

Figure 1:
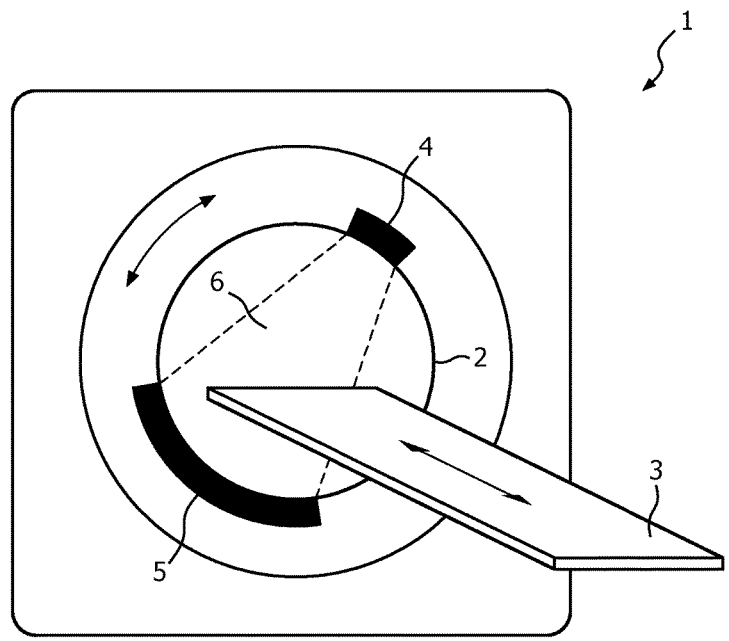
FIG. 1 shows a schematic representation of an illustrative computed tomography radiation imaging device.

FIG. 1 shows a highly schematic depiction of a computed tomography (CT) device 1. A radiation detector 5 and a photon source 4, in this embodiment an x-ray source, are mounted on a rotatable gantry 2. A subject to be scanned, such as a patient, is positioned on movable support 3, which during scanning moves through examination region 6, while gantry 2 rotates around the examination area and x-ray source 4 emits x-ray radiation. The x-ray radiation which passes through the subject is detected by radiation detector 5, in which the detected x-ray radiation is converted to electronic information that is further processed in further processing equipment (not shown) to visual information which is displayed to a user, such as a physician.

Figure 2:
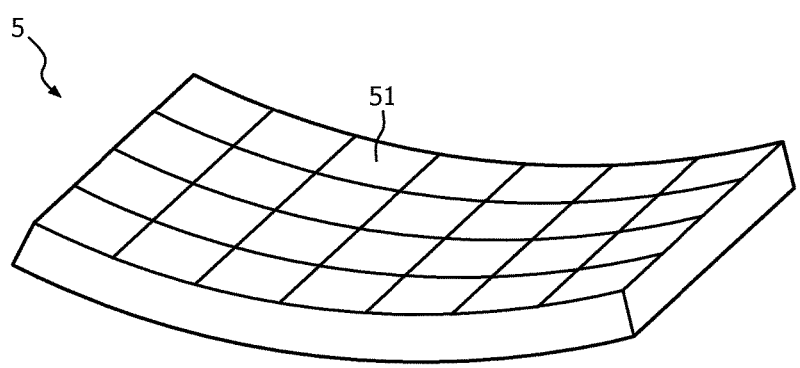
FIG. 2 shows a schematic representation of an illustrative curved radiation detector.

FIG. 2 is a highly schematic illustration of a radiation detector 5 of a CT device. The radiation detector is curved and is made up of several rows of individual sub-detectors 51 having several rows and columns of pixels. Each pixel detects a portion of incoming radiation. The radiation detector comprises a photon-electron conversion element in which incoming photons are converted to electrons that are then further analyzed. The photon-electron conversion element may comprise multiple sub-elements, such as a combination of a scintillator and a photodiode, or it may substantially be formed from a single element, such as in direct conversion detectors. The present invention is further explained, but not limited to, direct conversion radiation detectors.

In direct conversion radiation detectors a bulk of the direct photon conversion photon counting detector is formed by a direct conversion material layer. The direct conversion material layer may be composed of a single-crystal semiconductor material, which is an intrinsic material or has a (fully or partly depleted) p-i-n structure. $Cd_xZn_{1-x}Te$ (Cadmium Zinc Telluride, commonly abbreviated to CZT) is a suitable semiconductor material in light embodiments of the present invention. The direct conversion layer is placed between a detector cathode and a detector anode. The detector cathode is held at a negative bias potential, while the detector anode is held at a less repelling potential (usually approximately 0V). The detector cathode forms a continuous layer on the direct conversion material layer and is generally (semi)-transparent to photons with an energy level that are to be detected by the direct conversion photon counting detector. The detector anode is on the opposite side of the direct conversion layer and is made up from a grid of sub-detector 51.

When a photon passes the detector cathode and penetrates into the direct conversion material layer, the photon interacts with direct conversion material to generate numerous electron-hole pairs. The positively charged holes drift towards the strongly negatively charged detector cathode, while the negatively charged electrons drift towards the more positively charged detector anode. When the electrons approach detector anode, a signal is induced from each detector pixel, which, after collection, is indicative of a count of electrons that approached that particular electrode pixel. The generated signal is then further processed by processing units and eventually displayed on a display unit to a user as written information or as a reconstructed image of (part of) an examined body.

Figure 3A:
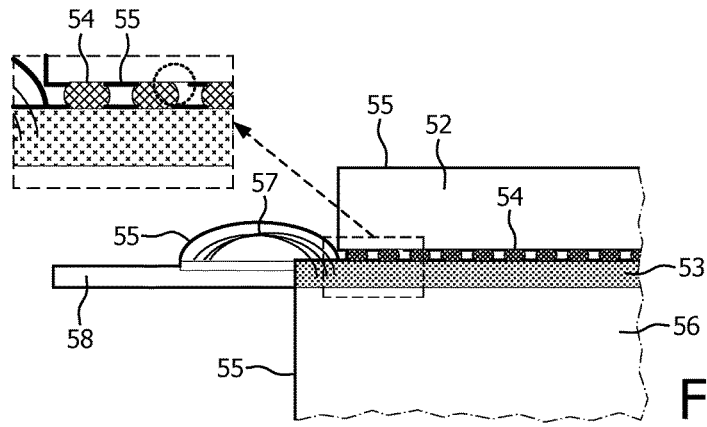
FIG. 3 shows an illustrative depiction of a cross-section of a radiation detector according to the prior art (3a) and two embodiments according to the present invention (FIG. 3b and FIG. 3c)

FIG. 3a presents an illustrative depiction of a cross-section of a sub-detector 51 according to the prior art, wherein a direct conversion layer 52, in this embodiment a CZT layer, is electrically and mechanically connected by electrical connections 54 to an ASIC 53 for handling and processing the detected radiation into signals that may be further processed. In this embodiment the electrical connections 54 are comprised of individual solder balls that are distributed between the direct conversion layer 52 and the ASIC 53. A skilled person would understand that other suitable electrical connection, such as columns, drops (e.g. silver-epoxy glue drops), etc., are also possible within the scope of the present invention. In this exemplary embodiment, the ASIC is mounted on a heat sink 56 and is connected to further processing electronic connection 58 (e.g. a flexible wire connector) by (encapsulated) wirebonds 57. The direct conversion layer 52 and ASIC 53, as well as the heat sink 56, wirebonds 57 and further processing electronics connection 58, are encapsulated by encapsulant layer 55. Encapsulation of the ASIC 53, heat sink 56, wirebonds 57 and further processing electronic connection 58 may be partial or even completely omitted in certain embodiments.

While the present invention is explained using electrical connections as the connection element, alternatively, for other detector types, such as those having scintillator-photodiode-ASIC combinations or other non-direct conversion detectors, the connection elements may also be optical connections (e.g. optical connections between a scintillator and photodiode) instead of or in addition to electrical elements. Also, there may be more than one (electrical or optical) connection element present. All these configurations are covered within the scope of this invention.

A method to construct the known radiation detector of FIG. 3a is schematically shown in FIG. 4a. First the direct conversion layer 52 and the ASIC 53 are conformally encapsulated by applying encapsulant layer 55 to the direct conversion layer 52 and ASIC 53. Next openings 551 are formed in the encapsulant layer 55 on opposing sides of the direct conversion layer 52 and ASIC 53, followed by applying the electrical connections 54 between the direct conversion layer 52 and the ASIC 53 at the locations op the openings 551. (Optional) encapsulation and attachment of the heat sink 56, wirebonds 57 and further processing electronic connection 58 may be performed simultaneously or separately. Also, as mentioned previously, in some embodiments only the direct conversion layer is (completely) encapsulated.

The known sub-detector 51 resulting from this method, and particularly the direct conversion layer 52 thereof, may still be somewhat sensitive to moisture, since moisture may still find a path along the (non-encapsulated) electrical connections 54 into the direct conversion layer 52, especially if the size and location of the formed openings 551 is sufficiently accurate or homogeneous or if or the alignment or size matching is not perfect with respect to the electrical connections 54. As an illustrative example, the second opening 551 from the left on the ASIC side was somewhat too large (as is more clearly shown in the circled area in the enlarged section). As such, the electrical connection 54 positioned left this opening 551 does not cover the full opening 551 leaving a non-encapsulated part of the surface of the direct conversion layer 52 through which moisture can freely penetrate into the direct conversion layer 52. Also moisture has direct access to and may degrade the electrical elements 54, which may, amongst others, cause delamination. While the defect was shown to be relatively large in this example (for clarity reasons), even a much smaller, pinhole-type, opening can already be quite detrimental to the moisture sensitivity of the direct conversion layer 52.

Figure 3B:
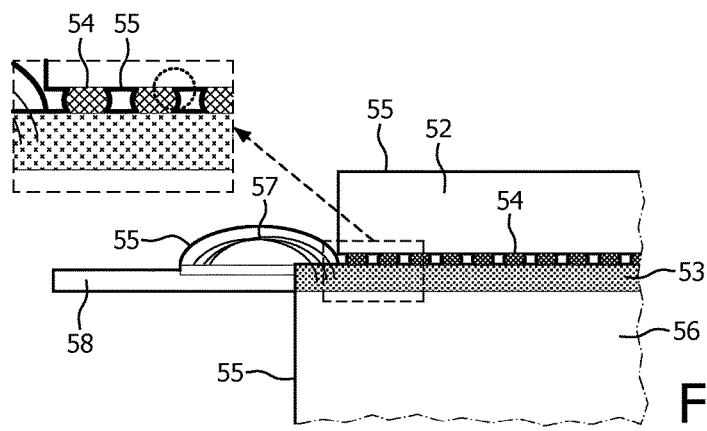

The present invention provides a radiation detector that does not have this drawback. A cross-section of a first embodiment of a radiation detector 5 according to the present invention is shown in FIG. 3b. In this embodiment the configuration is similar to that of FIG. 3a, but in this case also the outer surfaces of the electrical connections 54 are conformally encapsulated. Within the context of this invention the term 'outer surfaces' means all surfaces that are not in direct contact with a surface of another component of the radiation detector (excluding the encapsulation layer). Also the photon-electron conversion element 52 (in this embodiment again a direct conversion layer) is fully encapsulated. In this embodiment also the ASIC 53, the heat sink 56, wirebonds 57 and further processing electronic connection 58 are completely or partly encapsulated. This is however optional, for instance the heat sink 56 may not be completely encapsulated to allow for a better temperature transport or the ASIC 53 may not be (fully) encapsulated for practical production reasons.

The radiation detector 5 of the present invention has a better moisture resistance than the previously described known radiation detector, because by also encapsulating the electrical connections 54 there are less or even no open pathways for moisture to travel to the direct conversion layer 52. Potential openings in the encapsulation layer 55 on the direct conversion layer 52 would be more likely to be closed by or during the encapsulation 55 that is applied to the electrical connections 54 (as is more clearly shown in the circled area in the enlarged section, which may be compared to the enlarged section with FIG. 3a). A further advantage is that the radiation detector of the present invention can be encapsulated after construction of the various parts. This obviates the need to create openings 551 in the encapsulation layer 55, thereby reducing the amount of potential leakage sites and also protects electrical connection elements 54 from moisture degradation.

This method is illustrated in FIG. 4b. In this example the direct conversion layer 52 and the ASIC 53 are mechanically and electrically connected by applying electrical connections 54 between them to form a detector core assembly. This may be done by soldering, conductive gluing, deposition or any other known method. The electrical connections may be of any shape, but solder balls are particularly preferred, because they can be precisely, homogeneously and relatively quickly applied. Electrical connection elements comprising drops, particularly metal filled-epoxy drops (e.g. silver or copper filled), also are preferable for the same reasons. After the electrical connections 54 are established the direct conversion layer 52 and the electrical connections, and in this example also the ASIC, are simultaneously encapsulated by applying an encapsulant to the detector core assembly, ensuring a conformal coating around the detector core assembly. Since the encapsulated direct conversion material does not need to be opened up anymore, no additional (pin)-holes or other defects are introduced after encapsulation. Furthermore, compared to the known method, the method according to the present invention reduces the number of steps and is less complicated since there is no need to align the openings 55 of the direct conversion layer 52 with the openings 55 of the ASIC and with the electrical connections 54.

(II, II') is the parylene precursor material (often called the 'intermediate'), in this case a stabilized p-xylylene bi-radical, and (III) is parylene.

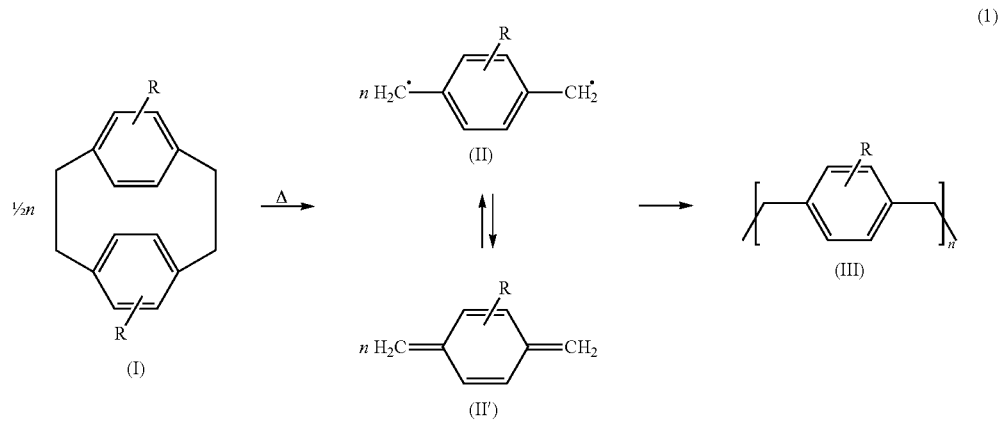

(1)

To be able to obtain a conformal coating that penetrates even within the small spaces between the electrical connections 54, it is highly preferable to use an encapsulant that is processable in the gas-phase, since a gas will easily penetrate even in the smallest spaces. As mentioned in the introduction of this document, most gas-phase processable materials are not suitable, since they require a high processing time for elongated periods of time, which will negatively influence the single crystal properties of direct conversion materials such as CZT, making them less effective and reliable in photon-electron conversion. At a temperature below 100 degrees Celsius the direct conversion material will remain relatively stable, especially when not exposed to this temperature for too long. It is preferred to remain under 60 degrees Celsius, to reduce degradation of the single crystal even further and to elongate potential exposure times. Most preferable is applying, e.g. depositing, the encapsulant material at room temperature. This not only reduces degradation even further, it also reduces mechanical stresses due to temperature differences and required energy consumption is limited.

As mentioned previously, parylene is a particularly suitable encapsulant. Within the context of this invention the term 'parylene' comprises all poly-p-xylylene polymers. The parylene may be substituted, e.g. with halogens such as parylene C, parylene D, parylene AF-4 or parylene VT-4, or with amines such as parylene A or parylene AM, or may be un-substituted (parylene N).

A parylene encapsulation layer 55 is formed by depositing a parylene precursor molecule on the direct conversion material 52 and the electrical connections 54 (and any other detector components to be encapsulated) in a depositing chamber. The parylene precursor material spontaneously polymerizes into parylene upon contact with the detector core assembly.

The parylene precursor material is preferably prepared in a reaction chamber near the deposition chamber and the parylene precursor material is added to the deposition chamber immediately after it has been formed.

Equation (1) depicts an exemplary reaction equation for the formation of the parylene precursor material and of parylene, in which (I) is a paracyclophane (often simply called the 'dimer'), optionally substituted with one or more substituents R, such as for instance a halogen or an amine, The dimer (I) is usually sublimated at approx. 175 degrees Celsius and then cracked into the reactive intermediate (II, II') at a temperature around 700 degrees Celsius. The gaseous intermediate (II, II') is brought into the deposition chamber where the detector core assembly is present and which is kept at room temperature. To avoid premature polymerization or dimerization it is preferably that the chamber in which the intermediate (II, II') is formed is (controllably) connected to the deposition chamber. The intermediate (II, II') physisorbs onto the detector core assembly and upon contact with the assembly and due to the rapid cooling the intermediate (II, II') polymerizes into parylene (III) forming a thin, conformal, moisture barrier parylene encapsulation layer 55 on the reaction core assembly.

A skilled person would understand that variations of this encapsulation process will also result in a suitable encapsulation material. For instance, he may change processing parameters and or amounts to influence layer thickness or processing times. He would also understand that a pretreatment (e.g. by a plasma, ozone, a solvent or an adhesion promoter, for instance a silane based adhesion promotor) of the detector core assembly may increase physisorption of the intermediate (II, II'), but care must be taken that the pretreatment does not degrade the direct conversion material.

Figure 5:
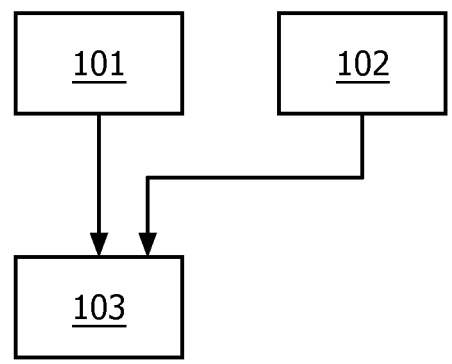
FIG. 5 shows a flow chart of a method to encapsulate a radiation detector according to the present invention.

FIG. 5 depicts a schematic illustration of a method to encapsulate a radiation detector core assembly. In step 101 the radiation detector core assembly is assembled by electrically and mechanically connecting a photon-electron conversion element 52 with an integrated circuit 53 using at least one electrical connection element 54 located between them. In step 102 an encapsulant material (such as a parylene precursor material) is prepared. In step 103 the encapsulation material is deposited at a temperature below 100 degrees Celsius onto at least the direct conversion material 52 and the electrical connections 54 to form a conformal layer.

Figure 3C:
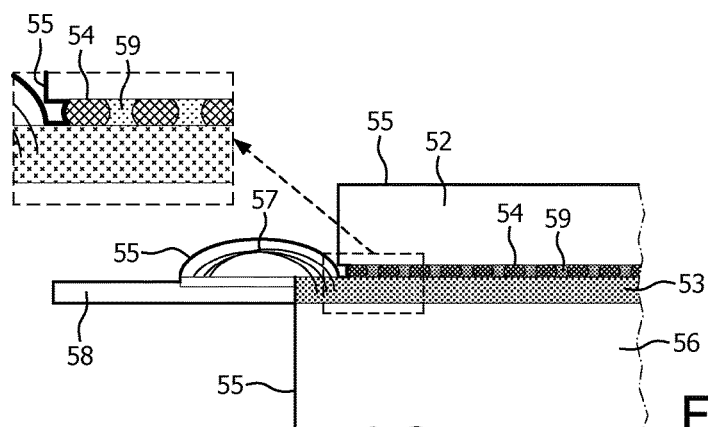

For structural or electrical separation the electrical connections 54 may be separated by a non-conductive filler material 59 (also known as an 'underfill'). In that case only the sides of the thusly formed electrical connection element form the outer surface and no gas is able (or necessary) to penetrate between the direct conversion layer 52 and the ASIC 53. On the other hand, the underfill 59 may cause additional mechanical stresses. This embodiment is schematically depicted in FIG. 3c.

The detector core assembly may be formed into a detector tile 51, which in turn may be formed into a radiation detector 5 for use in a radiation imaging device, for instance a medical or security radiation imager, a camera or an astrophysical device. Such a radiation detector is particularly useful as a detector for a computed tomography imaging system 1 which demands high precision and mechanical stability of the individual detector tiles 51 to ensure fast sensor operation.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. For instance, the embodiments shown in FIGS. 3b and 3c now allow for a three-side buttable detector tile, but the present invention would also work for a four-side buttable detector tile with the electronics 55, 57, 58 placed elsewhere in the detector tile configuration.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for constructing a radiation detector core assembly comprising steps of:
    assembling a radiation detector core assembly from a photon-electron conversion element, an integrated circuit and at least one connection element located between and mechanically connecting the photon-electron conversion element with the integrated circuit;
    depositing a gaseous encapsulation material onto the assembled detector core assembly on all outer surfaces of the photon-electron conversion element and all over of the at least one electrical connection elements at a temperature below 100 degrees centigrade such that the gaseous encapsulation material physically contacts the assembled detector core assembly on all outer surfaces of the photon-electron conversion element and all over of the at least one electrical connection elements.

2. The method according to claim 1, wherein the temperature is below 60 degrees Celsius.

3. The method according to claim 1, wherein depositing the gaseous encapsulation material is a parylene precursor material that forms a parylene encapsulation layer on the assembled detector core assembly during or after the depositing step.

4. The method according to claim 3, wherein the parylene precursor material is an optionally substituted, p-xylylene radical monomer that is formed from thermal decomposition of p-cyclophane.

5. The method according to claim 4, wherein the parylene precursor material is formed in a reaction chamber that is controllably connected to a deposition chamber in which the deposition step is performed.

6. The method according to claim 1, wherein the at least one connection element comprises an electrical connection element that electrically connects the photon-electron conversion element with the integrated circuit, such as a solder ball or a metal filled epoxy drop, and/or an optical connection element that optically connects the photon-electron conversion element with the integrated circuit.

7. A radiation detector core assembly comprising:
    a photon-electron conversion element;
    an integrated circuit; and
    at least one electrical connection element located substantially between and electrically and mechanically connecting the photon-electron conversion element with the integrated circuit; wherein the radiation detector core assembly comprises an encapsulating layer that is conformal to all outer surfaces of the photon-electron conversion element and all over of the at least one electrical connection elements, wherein the encapsulating layer comprises an encapsulating material that is processable at a gas-phase and physically contacts the assembled radiation detector core assembly on all outer surfaces of the photon-electron conversion element and all over of the at least one electrical connection elements.

8. The radiation detector core assembly according to claim 7, wherein the photon-electron conversion element at least substantially consists of a direct conversion material.

9. The radiation detector core assembly according to claim 7, wherein the encapsulating layer comprises an encapsulating material that is processable at a temperature below 100 degrees Celsius.

10. The radiation detector core assembly according to claim 7, wherein the at least one connection element comprises an electrical connection element that electrically connects the photon-electron conversion element with the integrated circuit, such as a solder ball or a metal filled epoxy drop, and/or an optical connection element that optically connects the photon-electron conversion element with the integrated circuit.

11. The radiation detector core assembly according to claim 7, comprising multiple detector core assemblies, forming a computed tomography radiation detector.

12. A radiation imaging device comprising the radiation detector core assembly according to claim 9.

13. A computed tomography imaging system comprising the radiation detector core assembly according to claim 11.

14. A radiation detector comprising the radiation core detector assembly according to claim 7.

* * * * *